US00PP29829P3

(12) United States Plant Patent
Probasco et al.

(10) Patent No.: US PP29,829 P3
(45) Date of Patent: Nov. 13, 2018

(54) HOP PLANT NAMED 'HBC 520'

(50) Latin Name: *Humulus lupulus*
Varietal Denomination: HBC 520

(71) Applicants: Eugene G. Probasco, Yakima, WA (US); Jason Perrault, Toppenish, WA (US)

(72) Inventors: Eugene G. Probasco, Yakima, WA (US); Jason Perrault, Toppenish, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 15/330,752

(22) Filed: Nov. 1, 2016

(65) Prior Publication Data

US 2017/0127591 P1 May 4, 2017

Related U.S. Application Data

(60) Provisional application No. 62/285,568, filed on Nov. 2, 2015.

(51) Int. Cl.
*A01H 5/00* (2018.01)

(52) U.S. Cl.
USPC ..... Plt./236
CPC ..... *A01H 5/00* (2013.01)

(58) Field of Classification Search
USPC ..... Plt./236
CPC ..... A01H 5/00
See application file for complete search history.

*Primary Examiner* — Kent L Bell
(74) *Attorney, Agent, or Firm* — Svendsen Legal, LLC

(57) ABSTRACT

A new hop plant named 'HBC 520' is disclosed. 'HBC 520' is used for its exceptional and unique aromatic qualities.

3 Drawing Sheets

Genus and species: *Humulus lupulus*.
Variety denomination: 'HBC 520'.

STATEMENT REGARDING FEDERALLY SPONSORED RESEARCH OR DEVELOPMENT

None

BACKGROUND OF THE INVENTION

'HBC 520' is a product of a controlled breeding program carried out by the inventors in the Yakima Valley of Washington State. 'HBC 520' was one of several seedlings resulting from controlled cross made in 2006 with female parent 'HBC 182' (unpatented) and male parent '986-2' (unpatented). A single plant of 'HBC 520' was selected in 2009, and in 2010 was expanded to 30 plants, which were planted in the area of Toppenish, Wash. The plants were observed and evaluated for several years, and in 2014 a 1 acre test plot of 'HBC 520' was established in the area of Moxee, Wash. Throughout several generations of asexual propagation, 'HBC 520' has been observed to retain its distinctive characteristics and remain true to type.

COMPARISON OF 'HBC 520' TO PARENT PLANT AND COMARISON CULTIVAR

'HBC 520' is distinguishable from its male parent '986-2' with flowers that develop into mature hop cones without producing pollen, while flowers of '986-2' produce pollen without developing into mature hop cones.

Table 1. below, sets forth some of the distinguishing characteristics of 'HBC 520' as compared to its female parent 'YCR 182', and to the 'Centennial' cultivar as a closely comparable cultivar.

TABLE 1

| | INSTANT CV. 'HBC 520' | PARENT 'YCR 182' | COMPARISON CV. 'CENTENNIAL' |
|---|---|---|---|
| Alpha (% of cone weight) | 11.3 | 14.5-18.5 | 7-12 |
| Beta (% of cone weight) | 5.3 | 4-5 | 3.5-5.5 |
| Co-humulone (% of alpha acids) | 22.00 | 25.5-30.5 | 23-27 |
| Total Oil (mL/100 g) | 2.00 | 3.4 | 1-3 |
| Myrcene (% of total oil) | 45.00 | 61.2 | 55-65 |
| Linalool (% of total oil) | 0.23 | 0.36 | 0.6-0.9 |
| Caryophyllene (% of total oil) | 20.91 | 7.65 | 5-7 |
| Farnesene (% of total oil) | 0.09 | <1.0 | <1.0 |
| Humulene (% of total oil) | 16.04 | 7 | 14-20 |
| Aroma Profile | vanilla, cedar, fruity | NA | lemon, floral |

BRIEF DESCRIPTION OF THE PHOTOGRAPHS

Figure 1:
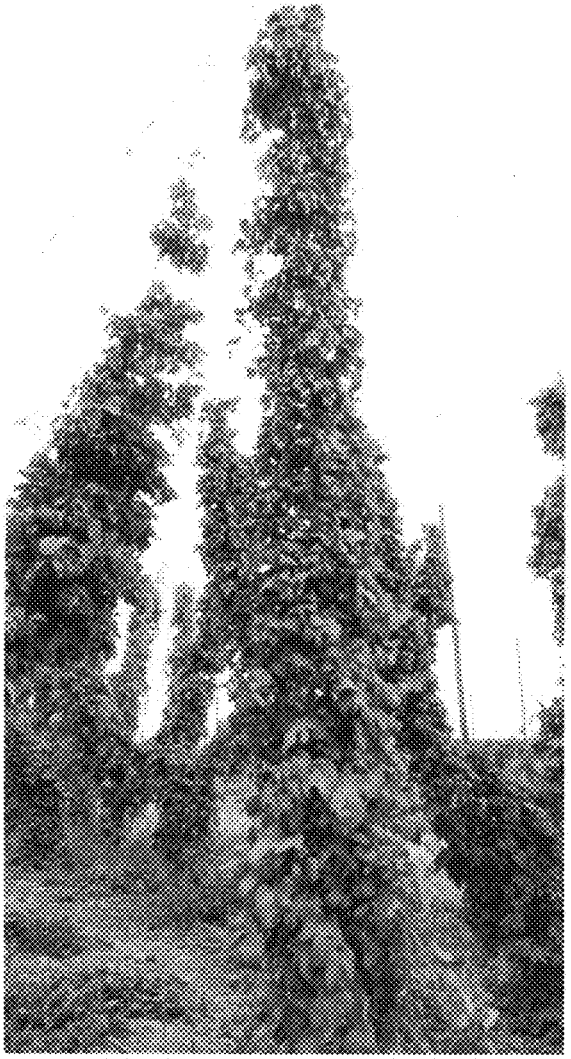
FIG. 1 illustrates a mature 'HBC 520' hop plant grown on a trellis.
Figure 2:
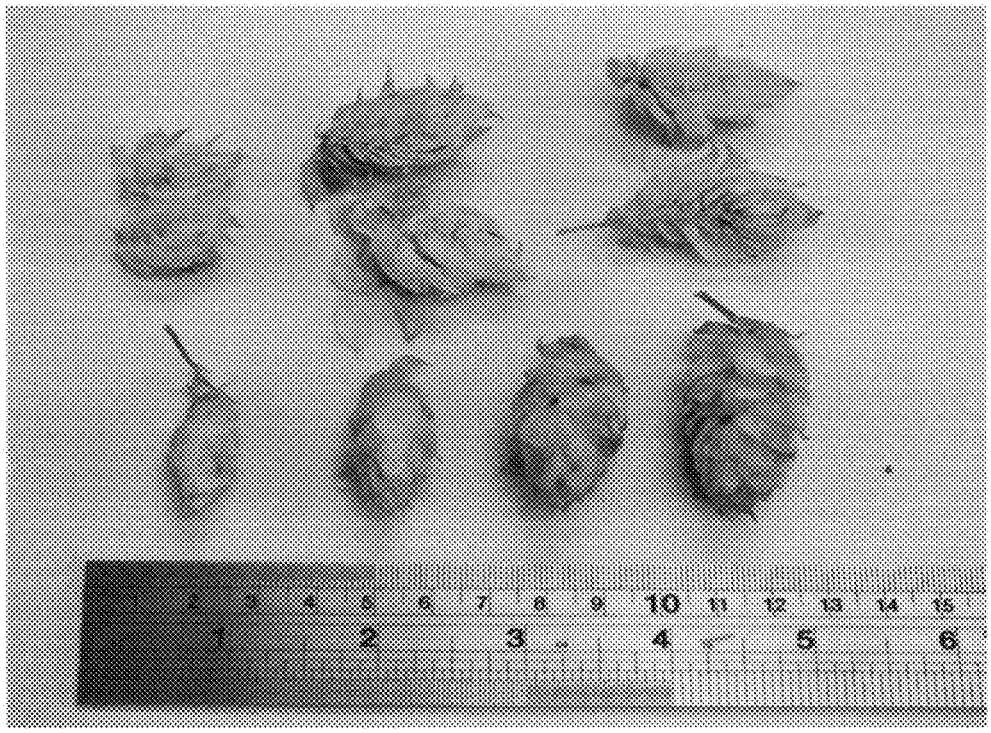
FIG. 2 illustrates whole cones and cross sections of cones of the 'HBC 520' hop plant.
Figure 3:
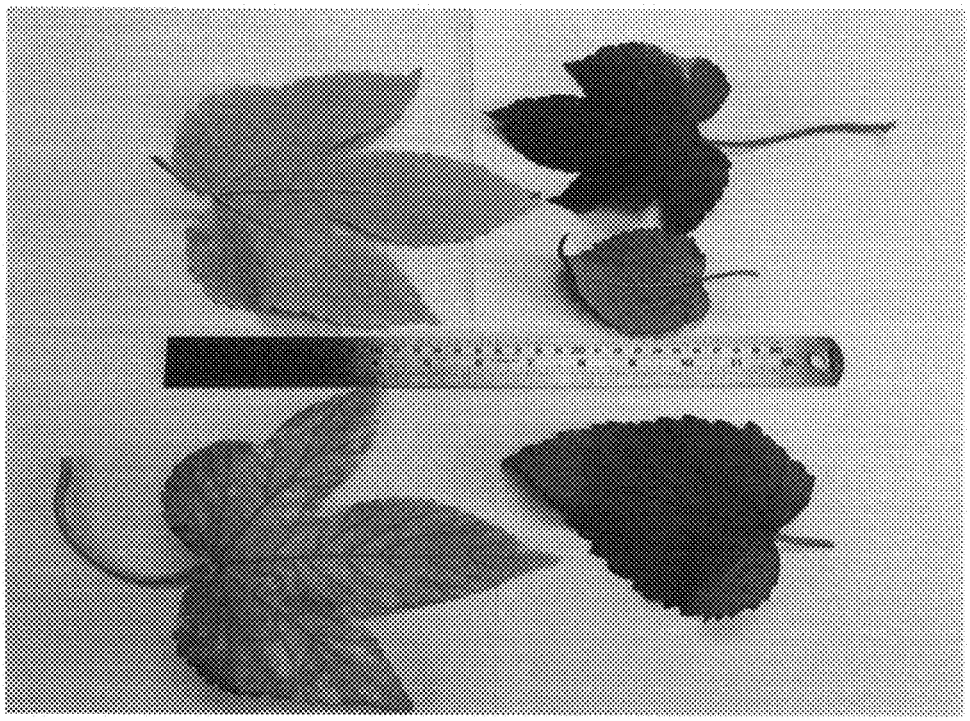
FIG. 3 illustrates the leaves of a mature 'HBC 520' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2009-2015 growing seasons at Toppenish, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. All color references are based on The Royal Horticultural Society Colour Chart.

Ploidy: Diploid (2n=2x).

Sex: Female.

Disease/pest resistance/susceptibility: Resistant to powdery mildew. Reaction to other common hop diseases unknown, none observed to date.

Use: Brewing beer and ale.

Harvest date: September (during 2009 to 2015 growing seasons at Toppenish, Wash.).

Crop yield: Approximately between 1,800 lbs per acre and 2,200 lbs per acre.

Plant shape: Climbing bine, columnar growth.

Quality characteristics (averages):

*Alpha acid* (*as % of cone weight*).—11.3%.
*Beta acid* (*as % of cone weight*).—5.3%.
*Cohumulone* (*as % of alpha acids*).—22%.
*Storageability* (*% loss*).—12%.

Oil analytical characteristics (averages):

*Total oil* (*ml/100 g of cones*).—2.00% Oil.
*A-pinene*.—0.09% Total Oil.
*B-pinene*.—0.59% Total Oil.
*Myrcene*.—45.00% Total Oil.
2-*methyl-butyl isobutyrate*.—0.66% Total Oil.
*Limonene*.—0.21% Total Oil.
*Linalool*.—0.23% Total Oil.
*Caryophyllene*.—20.91% Total Oil.
*Farnesene*.—0.09% Total Oil.
*Humulene*.—16.04% Total Oil.
*Citral*.—1.69% Total Oil.
*Geranyl acetate*.—0.09% Total Oil.
*Citronellol*.—1.39% Total Oil.
*Nerol*.—0.14% Total Oil.
*Geraniol*.—0.03% Total Oil.
*B-lonene*.—0.01% Total Oil.

Bine:

*Color*.—Yellow-Green 144D.
*Stripe present*.—No.
*Stipule direction*.—Horizontal.
*Stipule color*.—Yellow-Green N144A.
*Average number of stipule per bine*.—Two per node.
*Typical and observed bine length*.—Typical bine growth of 19 feet to 23 feet, when grown on a standard eighteen foot trellis.
*Internode length of bine*.—19 cm-23 cm.
*Bine diameter*.—10 mm at base; 11 mm at nine feet; 10 mm at terminal end of eighteen feet.

Lateral:

*Color*.—Yellow-Green 145C.
*Typical and observed lateral length*.—71 cm-93 cm.
*Internode length of laterals*.—11 cm-14 cm.
*Lateral diameter*.—3-5 mm at the base; and 0.5 mm to 1 mm at the terminal end.

Leaf:

*Arrangement*.—Opposite.
*Shape*.—Palmate.
*Leaf apex descriptor*.—Acuminate.
*Leaf base descriptor*.—Cordate.
*Average length of mature leaf*.—16.5 cm.
*Average width of mature leaf*.—17.5 cm.
*Color of mature leaf upper surface*.—Green 137 A.
*Color of mature leaf lower surface*.—Green 137A.
*Color of immature leaf upper surface*.—Green 137B.
*Color of immature leaf lower surface*.—Green 137 A.
*Number of lobes*.—5.
*Margin*.—Serrate.
*Serrations per inch*.—5.
*Average petiole length* (*mature*).—65 mm.
*Petiole diameter*.—4-5 mm.
*Petiole color*.—Yellow-Green 144 A.
*Petiole color at base*.—Yellow-Green 144A.
*Venation*.—Palmate.
*Vein color*.—Yellow-Green 145B.

Cone:

*Avg. length*.—40 mm.
*Avg. diameter*.—20 mm.
*Avg. weight*.—900 mg to 1100 mg.
*Pickability*.—Good.
*Bract tip color*.—Yellow-Green 144B.
*Bract base color*.—Yellow-Green 145C.
*Bract margin*.—Entire.
*Bract base*.—Rounded.
*Bracteole color* (*both surfaces*).—Yellow-Green 145C.
*Bracteole typical length*.—14 mm to 15 mm.
*Bracteole typical width*.—7 mm to 8 mm.
*Cone shape*.—Oblong.
*Bract shape*.—Orbicular.
*Bract tip shape*.—Oval.
*Bracteole shape*.—Ovate.
*Lupulin glands color*.—Yellow-Orange 17C.

What is claimed:

1. A new and distinct Hop plant as illustrated and described herein.

* * * * *